United States Patent [19]

Hubele

[11] Patent Number: 5,439,912
[45] Date of Patent: Aug. 8, 1995

[54] 2-PHENYLAMINO-4-CYANO-PYRIMIDINES

[75] Inventor: Adolf Hubele, Magden, Switzerland

[73] Assignee: Ciba-Geigy Corporation, Ardsley, N.Y.

[21] Appl. No.: 282,385

[22] Filed: Jul. 29, 1994

Related U.S. Application Data

[63] Continuation of Ser. No. 949,273, Sep. 21, 1992, abandoned, which is a continuation of Ser. No. 699,544, May 14, 1991, abandoned.

[30] Foreign Application Priority Data

May 17, 1990 [CH] Switzerland .................. 1668/90

[51] Int. Cl.⁶ .................. C07D 239/42; A01N 43/54
[52] U.S. Cl. .................. 514/275; 544/330; 544/332
[58] Field of Search ................. 514/275; 544/330, 332

[56] References Cited

U.S. PATENT DOCUMENTS

| | | | |
|---|---|---|---|
| 4,659,363 | 4/1987 | Hubele | 71/92 |
| 4,931,560 | 6/1990 | Hubele | 544/315 |
| 4,966,622 | 10/1990 | Rempfler | 71/92 |
| 4,997,941 | 3/1991 | Hubele | 544/332 |
| 5,159,078 | 10/1992 | Rempfler et al. | 544/330 |

FOREIGN PATENT DOCUMENTS

| | | |
|---|---|---|
| 224339 | 6/1987 | European Pat. Off. . |
| 0337943 | 10/1989 | European Pat. Off. . |
| 151404 | 10/1981 | Germany . |

*Primary Examiner*—John M. Ford
*Attorney, Agent, or Firm*—Edward McC. Roberts

[57] ABSTRACT

Compounds of formula

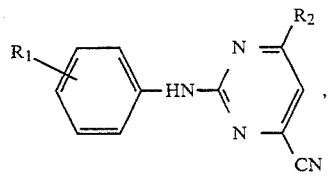

wherein $R_1$ is hydrogen, 3-fluorine or 4-fluorine, and $R_2$ is $C_1$–$C_4$alkyl, halo- or hydroxy-substituted $C_1$–$C_2$alkyl, $C_3$–$C_6$cycloalkyl or $C_3$–$C_6$cycloalkyl mono- to tri-substituted by identical or different substituents selected from methyl and halogen, have valuable microbicidal properties. The novel compounds can be used in crop protection for preventing an attack on cultivated plants by phytopathogenic microorganisms and for controlling those pests.

10 Claims, No Drawings

2-PHENYLAMINO-4-CYANO-PYRIMIDINES

This application is a continuation, of application Ser. No. 07/949,273, filed Sep. 21, 1992, now abandoned, which is a continuation of Ser. No. 07/699,544, filed May 14, 1991, which is now abandoned.

The present invention relates to novel 2-anilinopyrimidine derivatives of formula I below. It relates also to the preparation of those compounds and to agrochemical compositions that comprise at least one of those compounds as active ingredient. The invention relates also to the preparation of the said compositions and to the use of the compounds or compositions for controlling pests, especially harmful insects and plant-destructive microorganisms, especially fungi.

The compounds according to the invention have the general formula I

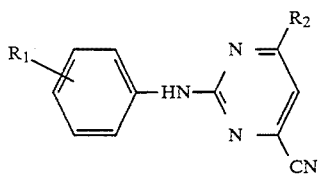 (I)

wherein $R_1$ is hydrogen, 3-fluorine or 4-fluorine, and $R_2$ is $C_1$–$C_4$alkyl, halo- or hydroxy-substituted $C_1$–$C_2$alkyl, $C_3$–$C_6$cycloalkyl or $C_3$–$C_6$cycloalkyl mono- to tri-substituted by identical or different substituents selected from methyl and halogen; including their acid addition salts and metal salt complexes.

Depending on the number of carbon atoms indicated, alkyl is to be understood as being, for example, methyl, ethyl, propyl, butyl and their isomers, for example isopropyl, isobutyl, tert-butyl or sec-butyl. Halogen is fluorine, chlorine, bromine or iodine, preferably chlorine. Depending on the number of carbon atoms indicated, cycloalkyl is, for example, cyclopropyl, cyclobutyl, cyclopentyl or cyclohexyl.

The invention relates both to the free compounds of formula I and to their addition salts with inorganic and organic acids as well as to their complexes with metal salts.

Salts according to the invention are especially addition salts with physiologically tolerable inorganic or organic acids, for example hydrohalic acids, for example hydrochloric, hydrobromic or hydriodic acid, sulfuric acid, phosphoric acid, phosphorous acid or nitric acid, or organic acids such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

Metal salt complexes of formula I comprise the basic organic molecule and an inorganic or organic metal salt, for example the halides, nitrates, sulfates, phosphates, acetates, trifluoroacetates, trichloroacetates, propionates, tartrates, sulfonates, salicylates, benzoates, etc. of the elements of the second main group, such as calcium and magnesium, and of the third and fourth main groups, such as aluminium, tin or lead, and of the first to eighth subgroups, such as chromium, manganese, iron, cobalt, nickel, copper, zinc, etc.. Preference is given to the subgroup elements of the 4th period. The metals may be in the various valencies associated with them. The metal complexes may be mono- or polynuclear, that is to say they may contain one or more organic molecular components as ligands.

The compounds of formula I are oils, resins or solids that are stable at room temperature and are distinguished by valuable microbicidal properties. They can be used in the agricultural sector or related fields preventively and curatively for controlling plant-destructive microorganisms. The compounds of formula I according to the invention are distinguished at low rates of application not only by excellent fungicidal activity, but also by the fact that they are especially well tolerated by plants.

The following groups of compounds are preferred on account of their marked microbicidal, especially phytofungicidal, activity.

Group 1: Compounds of formula I wherein:
  $R_1$ is hydrogen, 3-fluorine or 4-fluorine; and
  $R_2$ is $C_1$–$C_3$alkyl, cyclopropyl or cyclopropyl substituted by methyl or by chlorine.

Group 2: Compounds of formula I wherein:
  $R_1$ is hydrogen; and
  $R_2$ is methyl, ethyl, cyclopropyl or 2-methylcyclopropyl.

Group 3: Compounds of formula I wherein:
  $R_1$ is hydrogen, 3-fluorine or 4-fluorine; and
  $R_2$ is methyl, ethyl or cyclopropyl.

For use as fungicidal active ingredients, the following compounds may be mentioned as being especially preferred:

2-phenylamino-4-cyano-6-methylpyrimidine (comp. no. 1.1), 2-phenylamino-4-cyano-6-ethylpyrimidine (comp. no. 1.3), 2-phenylamino-4-cyano-6-cyclopropylpyrimidine (comp. no. 1.11) and 2-(3-fluorophenylamino)-4-cyano-6-methylpyrimidine (comp. no. 1.16).

N-pyrimidinylaniline compounds are already known. For example, in published European patent application 0 224 339 and DD patent specification 151 404, compounds having an N-2-pyrimidinyl structure are described as being effective against plant-destructive fungi. In addition, compounds having an anilinopyrimidine structure substituted by cyano groups have become known (see European Patent Application No. 0 337 943). According to the description, however, those compounds are used only as intermediates for the synthesis of herbicidally active urea derivatives. The known N-pyrimidinylaniline derivatives have hitherto been unable to meet the requirements made of them for use as fungicides, especially at low rates of application.

The compounds of formula I are prepared by 1.1 reacting a guanidine salt of formula IIa

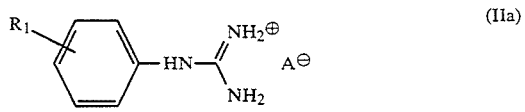 (IIa)

or a guanidine compound of formula IIb

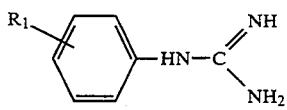

with a ketone of formula III

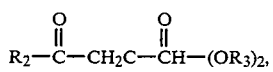

wherein $R_3$ is an alkyl radical, preferably $C_1$–$C_4$alkyl, and $A^\ominus$ is an acid anion, in a protic solvent or without a solvent, at temperatures of from 40° to 160° C., preferably from 60° to 110° C., to form a pyrimidine compound of formula IV

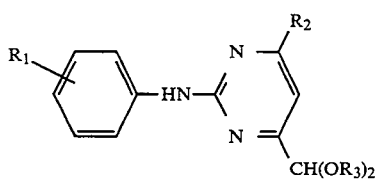

and 1.2 hydrolysing the resulting acetal of formula IV in the presence of an acid, for example a hydrohalic acid or sulfuric acid, in water or aqueous mixtures of inert solvents, for example alcohols or dimethylformamide, at temperatures of from 20° to 100° C., preferably from 30° to 60° C., to form the pyrimidinylaldehyde of formula V

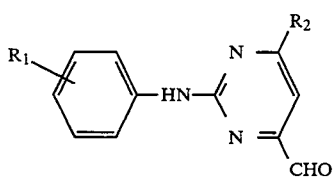

and 1.3 then converting the aldehyde of formula V with a hydroxylamine salt and a base that frees the hydroxylamine, in a protic solvent, preferably in the presence of water, at temperatures of from 10° to 90° C., preferably at from 10° C. to 60° C., into the oxime of formula VI

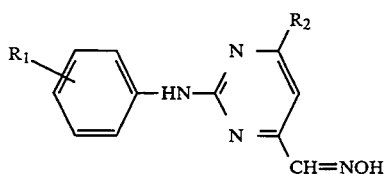

and 1.3.1 subjecting the oxime of formula VI to a reaction in which the elements of water are removed; the oxime, for example, being converted in an intermediate step into a compound of formula VII

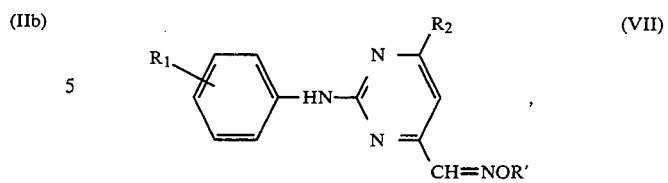

wherein R' is an acyl radical COR" a carbamoyl radical CONHR" or an oxycarbonyl radical COOR", in which R" is an alkyl radical, preferably $C_1$–$C_4$alkyl, and the compound of formula VII then being decomposed by removal of the acyl radical HOCOR" in inert solvents at temperatures of from 60° to 120° C., preferably from 60° to 100° C.; or 1.4 from the pyrimidinealdehyde of formula V, preparing the oxime of formula VI in an intermediate step by reaction in tertiary bases, for example pyridine and hydroxylamine salt, and forming the compound of formula I directly therefrom in situ by treatment with an acid halide or acid anhydride, for example acetic anhydride, at temperatures of from 40° to 120° C., preferably from 60° to 100° C.; or 2. reacting a compound of formula VIII

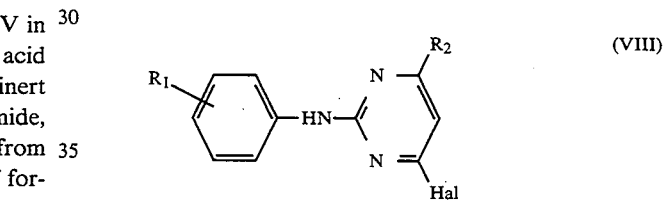

with a cyanide of formula IX

wherein Hal is fluorine, chlorine, bromine or iodine, preferably chlorine or iodine, and Me is an alkali metal cation, alkaline earth metal cation or heavy metal cation, preferably sodium, potassium or copper, in an aprotic solvent, for example dimethylformamide or dimethyl sulfoxide, at temperatures of from 60° to 160° C., preferably from 80° to 120° C.; or 3.1 cyclising urea of formula X

with a diketone of formula III

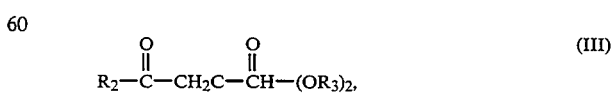

wherein $R_3$ is an alkyl radical, preferably $C_1$–$C_4$alkyl, in the presence of an acid in an inert solvent at temperatures of from 20° to 140° C., preferably from 20° to 40° C., to form a pyrimidine compound of formula XI

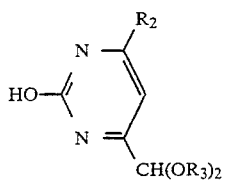

and 3.2 replacing the OH group in the compound of formula XI by halogen using excess PO(Hal)$_3$ in the presence or absence of an inert solvent at temperatures of from 50° to 110° C., preferably at the reflux temperature of the PO(Hal)$_3$, to form a compound of formula XII

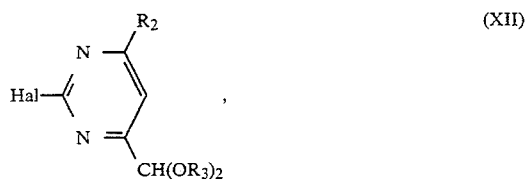

wherein Hal is halogen, preferably chlorine or bromine, and then 3.3 reacting a compound of formula XII with an aniline compound of formula XIII

either
a) in the presence of a proton acceptor, for example in an excess of the aniline compound of formula XIII or of an inorganic base, with or without an inert solvent, or
b) in the presence of an acid in an inert solvent, in each case at temperatures of from 60° to 120° C., preferably from 80° to 100° C., to form a compound of formula IV

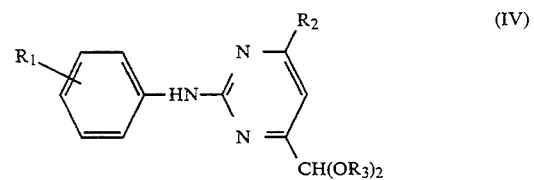

and converting the resulting acetal into a compound of formula I in the manner described under 1.2, 1.3 and 1.3.1, the radicals R$_1$ and R$_2$ in the above-described processes being as defined under formula I.

In the processes described, suitable salt radicals for the acid anion A$^\ominus$ in the compounds of formula IIa are, for example: carbonate, hydrogen carbonate, nitrate, halide, sulfate and hydrogen sulfate.

Halide is to be understood as meaning fluoride, chloride, bromide or iodide, preferably bromide or chloride.

The acids used are especially inorganic acids, for example hydrohalic acids, for example hydrofluoric acid, hydrochloric acid or hydrobromic acid, as well as sulfuric acid, phosphoric acid or nitric acid, but it is also possible to use suitable organic acids, such as acetic acid, toluenesulfonic acid, etc..

The proton acceptors used are, for example, inorganic or organic bases, for example alkali metal or alkaline earth metal compounds, for example the hydroxides, oxides or carbonates of lithium, sodium, potassium, magnesium, calcium, strontium and barium, or alternatively hydrides, for example sodium hydride. There may be mentioned as organic bases, for example, tertiary amines, such as triethylamine, triethylenediamine and pyridine.

In the processes described above, according to the reaction conditions, there may be used in addition to the solvents which have been mentioned, for example, the following:

Halogenated hydrocarbons, for example chlorinated hydrocarbons, such as tetrachloroethane, methylene chloride, chloroform, carbon tetrachloride, chlorobenzene, chlorotoluene, ethers, such as ethyl propyl ether, methyl tertbutyl ether, di-n-butyl ether, diisobutyl ether, diisoamyl ether, diisopropyl ether, diethyl ether, ethylene glycol dimethyl ether, tetrahydrofuran, dioxane, nitrated hydrocarbons, such as nitrobenzene, nitriles, such as acetonitrile, butyronitrile, aliphatic or cycloaliphatic hydrocarbons, such as heptane, hexane, petroleum fractions in a boiling point range of from 70° C. to 190° C., cyclohexane, petroleum ether, ligroin, esters, such as ethyl acetate, amides, for example formamide, dimethylformamide; ketones, such as acetone, methyl ethyl ketone; alcohols, especially lower aliphatic alcohols, for example methanol, ethanol, n-propanol, isopropanol and the isomers of the butanols; and water. Mixtures of the mentioned solvents and diluents are also suitable.

Methods of synthesis analogous to the above-described preparation processes have been published in the literature. There may be mentioned as references: A. Kreutzberger and J. Gillessen, J. Heterocyclic Chem. 22, 101 (1985); O. Stark, Ber. Dtsch. Chem. Ges. 42, 699 (1909); J. Hale, J. Am. Chem. Soc. 36, 104 (1914); G. M. Kosolapoff, J. Org. Chem. 26, 1895 (1961); St. Angerstein, Ber. Dtsch. Chem. Ges. 34, 3956 (1901); G. M. Kosolapoff, J. Org. Chem. 26, 1895 (1961); M. P. V. Boarland and J. F. W. McOmie, J. Chem. Soc. 1951, 1218; T. Matsukawa and K. Shirakuwa, J. Pharm. Soc. Japan 71, 933 (1951); Chem. Abstr. 46, 4549 (1952).

The described preparation processes, including all steps thereof, are included in the present invention.

The present invention relates also to the novel intermediates of formula V

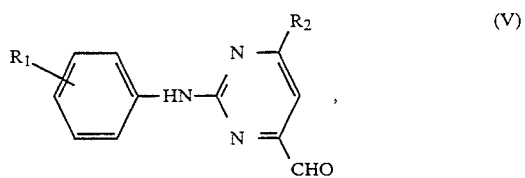

wherein R$_1$ is hydrogen, 3-fluorine or 4-fluorine, and R$_2$ is C$_1$–C$_4$alkyl or halo- or hydroxy-substituted C$_1$–C$_2$alkyl, and to the intermediates of formula VI

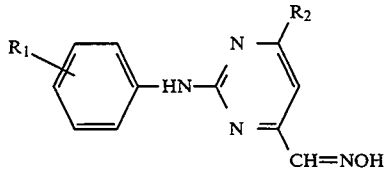

wherein $R_1$ is hydrogen, 3-fluorine or 4-fluorine, and $R_2$ is $C_1$–$C_4$alkyl, halo- or hydroxy-substituted $C_1$–$C_2$alkyl, $C_3$–$C_6$cycloalkyl or $C_1$–$C_4$cycloalkyl mono- to tri-substituted by identical or different substituents selected from methyl and halogen.

Surprisingly, it has been found that the compounds of formula I have, for practical field application purposes, a very advantageous biocidal spectrum against phytopathogenic microorganisms, especially fungi. Compounds of formula I have very advantageous curative, preventive and, in particular, systemic properties, and can be used for protecting numerous cultivated plants. With the compounds of formula I it is possible to inhibit or destroy the pests which occur on plants or on parts of plants (fruit, blossoms, leaves, stems, tubers, roots) in different crops of useful plants, while at the same time the parts of plants which grow later are also protected, for example, from attack by phytopathogenic microorganisms.

The compounds of formula I are effective, for example, against the phytopathogenic fungi belonging to the following classes: Fungi imperfecti (especially Botrytis, also Pyricularia, Helminthosporium, Fusarium, Septoria, Cercospora and Alternaria); Basidiomycetes (e.g. Rhizoctonia, Hemileia, Puccinia). They are also effective against the class of the Ascomycetes (e.g. Venturia and Erysiphe, Podosphaera, Monilinia, Uncinula) and of the Oomycetes (e.g. Phytophthora, Pythium, Plasmopara). They can also be used as dressing agents for protecting seeds (fruit, tubers, grains) and plant cuttings against fungus infections as well as against phytopathogenic fungi which occur in the soil.

The invention also relates to compositions comprising as active ingredient compounds of formula I, especially crop protection compositions, and to their use in the agricultural sector or related fields.

The present invention further embraces the preparation of those compositions, which comprises homogeneously mixing the active ingredient with one or more compounds or groups of compounds described herein. The invention furthermore relates to a method of treating plants, which comprises applying thereto the novel compounds of formula I or the novel compositions.

Target crops to be protected within the scope of the present invention comprise e.g. the following species of plants: cereals (wheat, barley, rye, oats, rice, maize, sorghum and related crops), beet (sugar beet and fodder beet), pomes, drupes and soft fruit (apples, pears, plums, peaches, almonds, cherries, strawberries, raspberries and blackberries), leguminous plants (beans, lentils, peas, soybeans), oil plants (rape, mustard, poppy, olives, sunflowers, coconut, castor oil plants, cocoa beans, groundnuts), cucumber plants (cucumber, marrows, melons), fibre plants (cotton, flax, hemp, jute), citrus fruit (oranges, lemons, grapefruit, mandarins), vegetables (spinach, lettuce, asparagus, cabbages, carrots, onions, tomatoes, potatoes, paprika), lauraceae (avocados, cinnamon, camphor), or plants such as tobacco, nuts, coffee, sugar cane, tea, pepper, vines, hops, bananas and natural rubber plants, as well as ornamentals.

The compounds of formula I are normally applied in the form of compositions and can be applied to the crop area or plant to be treated, simultaneously or in succession, with further compounds. These further compounds can be fertilisers or micronutrient donors or other preparations that influence plant growth. They can also be selective herbicides as well as insecticides, fungicides, bactericides, nematicides, molluscicides or mixtures of several of these preparations, if desired together with further carriers, surfactants or other application-promoting adjuvants customarily employed in formulation technology.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

A preferred method of applying a compound of formula I, or an agrochemical composition which comprises at least one of said compounds, is foliar application. The number of applications and the rate of application depend on the risk of infestation by the corresponding pathogen. However, the compounds of formula I can also penetrate the plant through the roots via the soil (systemic action) if the locus of the plant is impregnated with a liquid formulation, or if the compounds are applied in solid form to the soil, e.g. in granular form (soil application). In paddy rice crops, such granules may be applied in metered amounts to the flooded rice field. The compounds of formula I may, however, also be applied to seeds (coating) either by impregnating the seeds with a liquid formulation comprising a compound of formula I, or by coating them with a solid formulation.

The compounds of formula I are used in unmodified form or, preferably, together with the adjuvants conventionally employed in formulation technology, and are for this purpose advantageously formulated in known manner e.g. into emulsifiable concentrates, coatable pastes, directly sprayable or dilutable solutions, dilute emulsions, wettable powders, soluble powders, dusts, granules, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application for direct treatment of the plants or for soil treatment are normally from 50 g to 5 kg of active ingredient (a.i.) per hectare, preferably from 100 g to 2 kg a.i./ha, most preferably from 200 g to 600 g a.i./ha. The amounts of active ingredient used for seeds that are dressed and then sown are markedly lower, being the equivalent of from 0.1 g a.i./ha to 500 g a.i./ha, i.e. the amounts of active ingredient to be found together with the seed in an area of 1 ha. An amount of from 0.5 g a.i./ha to 100 g a.i./ha is preferred.

The formulations, i.e. the compositions, preparations or mixtures comprising the compound (active ingredient) of formula I and, where appropriate, a solid or liquid adjuvant, are prepared in known manner, e.g. by homogeneously mixing and/or grinding the active ingredients with extenders, e.g. solvents, solid carriers and, where appropriate, surfaceactive compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used, e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic nature can be used, e.g. especially dolomite or pulverised plant residues.

Particularly advantageous application-promoting adjuvants which are able to reduce substantially the rate of application are also natural (animal or vegetable) or synthetic phospholipids of the series of the cephalins and lecithins, which can be obtained e.g. from soybeans.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil. Mention may also be made of fatty acid methyllaurin salts.

More frequently, however, so-called synthetic surfactants are used, especially alkanesulfonates, fatty alcohol sulfates, sulfonated benzimidazole derivatives or alkylsulfonates.

The fatty alcohol sulfonates or sulfates are usually in the form of alkali metal salts, alkaline earth metal salts or unsubstituted or substituted ammonium salts and contain a $C_8$–$C_{22}$ alkyl radical, which also includes the alkyl moiety of acyl radicals, e.g. the sodium or calcium salt of lignosulfonic acid, of dodecyl sulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde.

Also suitable are corresponding phosphates, e.g. salts of the phosphoric acid ester of an adduct of p-nonylphenol with 4 to 14 mol of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediaminopolypropylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethyleneethanol, polyethylene glycol and octylphenoxypolyethoxyethanol.

Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methyl sulfates or ethyl sulfates, e.g. stearyltrimethylammonium chloride or benzyldi(2-chloroethyl)ammonium bromide.

Further surfactants customarily employed in formulation technology are known to the person skilled in the art or can be taken from the relevant specialist literature.

The agrochemical compositions usually comprise 0.1 to 99%, preferably 0.1 to 95%, of a compound of formula I, 99.9 to 1% preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

The compositions may also comprise further auxiliaries such as stabilisers, antifoams, viscosity regulators, binders, tackifiers as well as fertilisers or other active ingredients for obtaining special effects.

The following Examples serve to illustrate the invention in greater detail, but do not limit the invention.

1. Preparation Examples

EXAMPLE 1.1

Preparation of the intermediate 2-anilino-4-formyldiethylacetal-6-methylpyrimidine

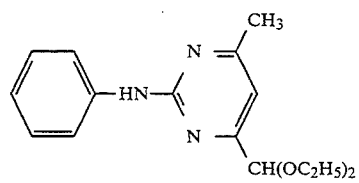

11.8 g (60 mmol) of phenylguanidine hydrogen carbonate and 12 g (64 mmol) of 1-methyl-3-formyldiethylacetal-1,3-propanedione in 80 ml of ethanol are heated under reflux for 4 hours with stirring, the evolution of carbon dioxide subsiding as the reaction progresses.

After cooling, the ethanol is largely evaporated off and the residue is taken up in 30 ml of diethyl ether, washed three times with 30 ml of water each time, dried over sodium sulfate and filtered, and the diethyl ether is evaporated off. The dark brown oil that remains is dissolved in 350 ml of petroleum ether (b.p. 40°-60° C.) at elevated temperature, heated under reflux for 10 minutes in the presence of activated carbon, cooled to approximately 40° C. and filtered over Hyflo, and concentrated to a volume of approximately 30 ml. The resulting yellowish crystals are isolated by filtration and melt at 63°-65° C.

EXAMPLE 1.2

Preparation of the intermediate 2-anilino-4-formyl -6-methylpyrimidine

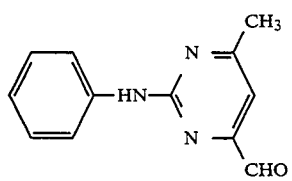

3 g (10.4 mmol) of 2-anilino-4-formyldiethylacetal-6-methylpyrimidine and 1 g of concentrated hydrochloric acid in 30 ml of water are stirred at 45° C. for 24 hours and then cooled to 15° C., and the pH is adjusted to 8 with sodium hydrogen carbonate solution. The light-brown powder is isolated by filtration and then washed with water and recrystallised from 70 ml of acetonitrile. The yellow crystals melt at 130°-131° C.

EXAMPLE 1.3

Preparation of 2-phenylamino-4-cyano-6-methylpyrimidine

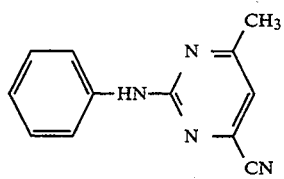

[comp. no. 1.1]

11.8 g (0.17 mol) of hydroxylamine hydrochloride are added in portions over a period of 5 minutes, with stirring, to 21.3 g (0.1 mol) of 2-anilino-4-formyl-6-methylpyrimidine in 90 ml of pyridine, the temperature rising to 40° C. After stirring at 50° C. for half an hour, 40 ml of acetic anhydride are added dropwise over a period of a quarter of an hour, the temperature rising to 70° C. After stirring at 90° C. for 3 hours, the reaction mixture is cooled and then concentrated in vacuo, and the dark brown oily residue is poured onto 600 ml of ice-water and adjusted to pH 8 with dilute sodium hydroxide solution. After extracting three times with 150 ml of ethyl acetate each time, the combined extracts are washed twice with 50 ml of water each time, dried over sodium sulfate and filtered, and the solvent is evaporated off. The dark brown oily residue is dissolved in 200 ml of tetrahydrofuran, treated with activated carbon and filtered, and the solvent is evaporated off. The brownish solid that remains is recrystallised twice from diisopropyl ether/methanol. The yellow crystalline powder melts at 125°-126° C.

EXAMPLE 1.4

Preparation of the intermediate 2-anilino-4-oximino-6-cyclopropylpyrimidine

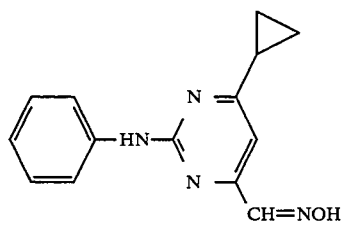

First 3.6 g (52 mmol) of hydroxylamine hydrochloride and then 2.8 g (26.4 mmol) of soda in 15 ml of water are added in portions over a period of a quarter of an hour, at room temperature and with stirring, to 10 g (42 mmol) of 2-anilino-4-formyl-6-cyclopropylpyrimidine in 150 ml of ethanol, and the mixture is then stirred at room temperature for 24 hours. The yellowish suspension is diluted with 50 ml of water, filtered and then washed with 10 ml of water, and the yellow semi-crystalline residue is recrystallised from 120 ml of ethanol. The beige crystals melt at 175°-185° C.

EXAMPLE 1.5

Preparation of 2-phenylamino-4-cyano-6-cyclopropylpyrimidine

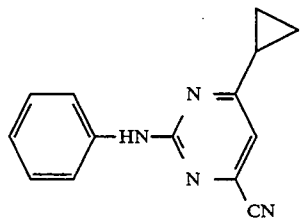

[comp. no. 1.11]

3 g (53 mmol) of methyl isocyanate in 10 ml of dioxane are added dropwise at room temperature over a period of 10 minutes, with stirring, to 7.6 g (30 mmol) of 2-anilino-4-oximino-6-cyclopropylpyrimidine and 200 mg of 1,4-diazabicyclo[2.2.2]octane in 60 ml of dioxane. After stirring at 75° C. for 16 hours, the mixture is cooled, the solvent is evaporated off and the light-brown oil that remains is purified by column chromatography over silica gel (toluene/diethyl ether: 3/2). After the eluant mixture has been evaporated off, the yellow solid is purified by recrystallisation from diisopropyl ether. The yellow crystals melt at 122°-125° C.

The following compounds of formula I can be prepared in that manner or in accordance with one of the methods indicated above.

TABLE 1

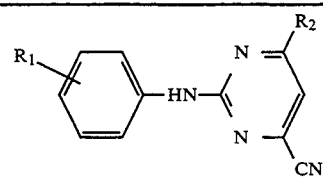

| Comp. no. | $R_1$ | $R_2$ | Physical constant |
|---|---|---|---|
| 1.1 | H | —$CH_3$ | m.p. 125–126°C. |

TABLE 1-continued

Structure: R1-phenyl-NH-pyrimidine with R2 and CN substituents

| Comp. no. | R₁ | R₂ | Physical constant |
|---|---|---|---|
| 1.2 | 3-F | 1-methylcyclopropyl (CH₃) | |
| 1.3 | H | —C₂H₅ | |
| 1.4 | 3-F | —C₃H₇-n | |
| 1.5 | 3-F | 1-chlorocyclopropyl (Cl) | |
| 1.6 | H | —C₃H₇-n | |
| 1.7 | 4-F | —CH₃ | m.p. 140–141° C. |
| 1.8 | H | —C₃H₇-i | |
| 1.9 | 3-F | 2-methylcyclopropyl (CH₃) | |
| 1.10 | 3-F | —C₂H₅ | |
| 1.11 | H | cyclopropyl | m.p. 122–125° C. |
| 1.12 | 4-F | —C₂H₅ | |
| 1.13 | 3-F | cyclohexyl | |
| 1.14 | H | cyclobutyl | |
| 1.15 | H | cyclopentyl | |
| 1.16 | 3-F | —CH₃ | m.p. 135–136° C. |
| 1.17 | 4-F | 2-methylcyclopropyl (CH₃) | |
| 1.18 | H | cyclohexyl | |
| 1.19 | 3-F | cyclopentyl | |
| 1.20 | 4-F | —C₃H₇-n | |
| 1.21 | H | 1-methylcyclopropyl (CH₃) | |
| 1.22 | 3-F | cyclobutyl | |
| 1.23 | H | 1-chlorocyclopropyl (Cl) | |
| 1.24 | 4-F | cyclopropyl | |
| 1.25 | 3-F | cyclopropyl | |
| 1.26 | 4-F | 1-methylcyclopropyl (CH₃) | |
| 1.27 | H | 2-methylcyclopropyl (CH₃) | |
| 1.28 | 3-F | —C₃H₇-i | |
| 1.29 | 4-F | 1-chlorocyclopropyl (Cl) | |
| 1.30 | H | —C₄H₉i | |
| 1.31 | H | —C₄H₉sec | |

TABLE 2

Novel intermediates of formula V

Structure: R1-phenyl-HN-pyrimidine with R2 and CHO substituents

| Comp. no. | R₁ | R₂ | Physical constant |
|---|---|---|---|
| 2.01 | H | CH₃ | m.p. 130–131° C. |
| 2.02 | 3-F | CH₃ | |
| 2.03 | 4-F | CH₃ | |
| 2.04 | H | C₂H₅ | |
| 2.05 | 3-F | C₂H₅ | |
| 2.06 | 4-F | C₂H₅ | |
| 2.07 | H | nC₃H₇ | |
| 2.08 | 3-F | nC₃H₇ | |
| 2.09 | 4-F | nC₃H₇ | |
| 2.10 | H | isocC₃H₇ | |
| 2.11 | 3-F | isocC₃H₇ | |
| 2.12 | 4-F | isocC₃H₇ | |
| 2.13 | H | nC₄H₉ | |
| 2.14 | 3-F | nC₄H₉ | |

TABLE 2-continued

Novel intermediates of formula V

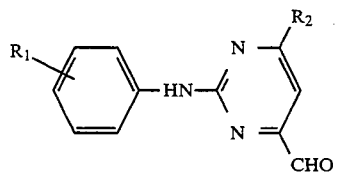

| Comp. no. | R₁ | R₂ | Physical constant |
|---|---|---|---|
| 2.15 | 4-F | nC₄H₉ | |
| 2.16 | H | isocC₄H₉ | |
| 2.17 | 3-F | isocC₄H₉ | |
| 2.18 | 4-F | isocC₄H₉ | |
| 2.19 | H | secC₄H₉ | |
| 2.20 | 3-F | secC₄H₉ | |
| 2.21 | 4-F | secC₄H₉ | |
| 2.22 | H | tertC₄H₉ | |
| 2.23 | 3-F | tertC₄H₉ | |
| 2.24 | 4-F | tertC₄H₉ | |

TABLE 1

Novel intermediates of formula VI

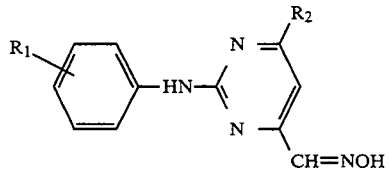

| Comp. no. | R₁ | R₂ | Physical constant |
|---|---|---|---|
| 3.1 | H | —CH₃ | m.p. 240–241°C. |
| 3.2 | 3-F | cyclopropyl-CH₃ | |
| 3.3 | H | —C₂H₅ | |
| 3.4 | 3-F | —C₃H₇-n | |
| 3.5 | 3-F | cyclopropyl-Cl | |
| 3.6 | H | —C₃H₇-n | |
| 3.7 | 4-F | —CH₃ | |
| 3.8 | H | —C₃H₇-i | |
| 3.9 | 3-F | cyclopropyl-CH₃ | |
| 3.10 | 3-F | —C₂H₅ | |
| 3.11 | H | cyclopropyl | m.p. 175–185° C. |
| 3.12 | 4-F | —C₂H₅ | |
| 3.13 | 3-F | cyclohexyl | |
| 3.14 | H | cyclobutyl | |

TABLE 1-continued

Novel intermediates of formula VI

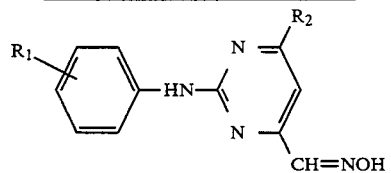

| Comp. no. | R₁ | R₂ | Physical constant |
|---|---|---|---|
| 3.15 | H | cyclopentyl | |
| 3.16 | 3-F | —CH₃ | |
| 3.17 | 4-F | cyclopropyl-CH₃ | |
| 3.18 | H | cyclohexyl | |
| 3.19 | 3-F | cyclopentyl | |
| 3.20 | 4-F | —C₃H₇-n | |
| 3.21 | H | cyclopropyl-CH₃ | |
| 3.22 | 3-F | cyclobutyl | |
| 3.23 | H | cyclopropyl-Cl | |
| 3.24 | 4-F | cyclopropyl | |
| 3.25 | 3-F | cyclopropyl | |
| 3.26 | 4-F | cyclopropyl-CH₃ | |
| 3.27 | H | cyclopropyl-CH₃ | |
| 3.28 | 3-F | —C₃H₇-i | |
| 3.29 | 4-F | cyclopropyl-Cl | |
| 3.30 | H | —C₄H₉i | |
| 3.31 | H | —C₄H₉sec | |

2. Formulation Examples for solid active ingredients of formula I (throughout, percentages are by weight)

| 2.1. Wettable powders | a) | b) | c) |
|---|---|---|---|
| a compound of Table 1 | 25% | 50% | 75% |
| sodium lignosulfonate | 5% | 5% | — |
| sodium lauryl sulfate | 3% | — | 5% |
| sodium diisobutylnaphthalene-sulfonate | — | 6% | 10% |
| octylphenol polyethylene glycol ether (7-8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| 2.2. Emulsifiable concentrate | |
|---|---|
| a compound of Table 1 | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| cyclohexanone | 34% |
| xylene mixture | 50% |

Emulsions of any required concentration can be obtained from this concentrate by dilution with water.

| 2.3. Dusts | a) | b) |
|---|---|---|
| a compound of Table 1 | 5% | 8% |
| talcum | 95% | — |
| kaolin | — | 92% |

Ready-for-use dusts are obtained by mixing the active ingredient with the carrier and grinding the mixture in a suitable mill.

| 2.4. Extruder granules | |
|---|---|
| a compound of Table 1 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| 2.5. Coated granules | |
|---|---|
| a compound of Table 1 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| 2.6. Suspension concentrate | |
|---|---|
| a compound of Table 1 | 40% |
| ethylene glycol | 10% |
| nonylphenol polyethylene glycol ether (15 mol of ethylene oxide) | 6% |

-continued

| 2.6. Suspension concentrate | |
|---|---|
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

EXAMPLE 3.1

Action against *Venturia inaegualis* on apple shoots
Residual-protective action

Apple cuttings with 10–20 cm long fresh shoots are sprayed with a spray mixture (0.006% active ingredient) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab infestation is evaluated 15 days after infection.

Compounds of Table 1 exhibit good activity against Venturia (less than 20% infestation). On the other hand, Venturia infestation is 100% on untreated and infected control plants.

EXAMPLE 3.2

Action against *Botrytis cinerea* on apples Residual-protective action

Artificially damaged apples are treated by grafting onto the damaged sites a spray mixture (0.002% active ingredient) prepared from a wettable powder formulation of the test compound. The treated fruits are then inoculated with a spore suspension of the fungus and incubated for one week at high humidity and about 20° C. Evaluation is made by counting the rotted damaged sites and deriving the fungicidal activity of the test compound therefrom.

Compounds of Table 1 exhibit good activity against Botrytis (less than 20% infestation). Thus e.g. compounds nos. 1.1 and 1.11 reduce Botrytis infestation to 0 to 10%. On the other hand, Botrytis infestation is 100% on untreated and infected control plants.

EXAMPLE 3.3

Action against *Erysiphae graminis* on barley
a) Residual-protective action

Barley plants about 8 cm in height are sprayed with a spray mixture (0.006% active ingredient) prepared from a wettable powder formulation of the test compound. The treated plants are dusted with conidia of the fungus after 3 to 4 hours. The infected barley plants are stood in a greenhouse at about 22° C. The fungus infestation is evaluated after 10 days.

Compounds of Table 1 exhibit good activity against Erysiphae (less than 20% infestation). On the other hand, Erysiphae infestation is 100% on untreated and infected control plants.

EXAMPLE 3.4

Action against *Helminthosporium gramineum*

Wheat grains are contaminated with a spore suspension of the fungus and dried. The contaminated grains are dressed with a suspension of the test compound prepared from a wettable powder (600 ppm of active ingredient, based on the weight of the seeds). Two days later the grains are placed in suitable agar dishes and the development of fungus colonies around the grains is assessed after a further four days. The effectiveness of the test compound is evaluated on the basis of the number and size of the colonies. The compounds of the Table substantially prevent fungus infestation (0 to 10% fungus infestation).

EXAMPLE 3.5

Action against *Colletotrichum lagenarium* on cucumbers

After a cultivation period of two weeks, cucumber plants are sprayed with a spray mixture (concentration 0.002%) prepared from a wettable powder formulation of the test compound. After two days, the plants are infected with a spore suspension ($1.5 \times 10^5$ spores/ml) of the fungus and incubated for 36 hours at 23° C. and high humidity. Incubation is then continued at normal humidity and about 22°–23° C. Evaluation of fungus infestation is made 8 days after infection. Fungus infestation is 100% on untreated and infected control plants.

Compounds of Table 1 exhibit good activity and inhibit the spread of the disease. Fungus infestation is reduced to 20% or less.

What is claimed is:

1. A compound of formula I

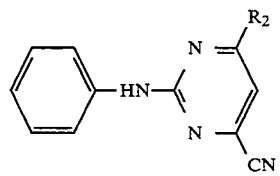

wherein $R_2$ is $C_1$–$C_4$alkyl; or an acid addition salt or metal salt complex thereof.

2. A compound of formula I according to claim 1 wherein $R_2$ is $C_1$–$C_3$alkyl.

3. A compound of formula I according to claim 1, wherein $R_2$ is methyl or ethyl.

4. A compound of formula I according to claim 1, wherein $R_2$ is methyl.

5. A composition for protecting plants from attack by microorganisms, which comprises a microbicidally effective amount of a compound of claim 1 and a carder.

6. A composition for protecting plants from attack by microorganisms, which comprises a microbicidally effective amount of a compound of claim 2 and a carrier.

7. A method of protecting plants against attack by phytopathogenic microorganisms, which comprises applying a microbicidally effective amount of a compound of claim 1 to a plant or to the locus of the plant.

8. A method of protecting plants against attack by phytopathogenic microorganisms, which comprises applying a microbicidally effective amount of a compound of claim 2 to a plant or to the locus of the plant.

9. A method of claim 7 wherein the phytopathogenic microorganisms are fungi.

10. A method of claim 8 wherein the phytopathogenic microorganisms are fungi.

* * * * *